US00PP31559P3

(12) United States Plant Patent
Kleynhans

(10) Patent No.: US PP31,559 P3
(45) Date of Patent: Mar. 17, 2020

(54) ***LACHENALIA* JACQ. F. EX MURRAY PLANT NAMED 'RADIENT'**

(50) Latin Name: ***Lachenalia* Jacq. f. ex Murray**
Varietal Denomination: Radient

(71) Applicant: AGRICULTURAL RESEARCH COUNCIL, Pretoria (ZA)

(72) Inventor: Riana Kleynhans, Benoni (ZA)

(73) Assignee: Agricultural Research Council, Pretoria (ZA)

( * ) Notice: Subject to any disclaimer, the term of this patent is extended or adjusted under 35 U.S.C. 154(b) by 0 days.

(21) Appl. No.: 14/756,820

(22) Filed: Oct. 19, 2015

(65) Prior Publication Data

US 2017/0112039 P1 Apr. 20, 2017

(51) Int. Cl.
*A01H 5/02* (2018.01)
*A01H 6/12* (2018.01)

(52) U.S. Cl.
USPC ..... Plt./263.1
CPC ..... *A01H 6/12* (2018.05)

(58) Field of Classification Search
USPC ..... Plt./263.1
See application file for complete search history.

(56) References Cited

PUBLICATIONS

UPOV hit on *Lachenalia* plant named 'Radient', ZA PBR ZA20104395, published 2010.*
ARC*LNR *Lachenalia* and other Flower bulb cultivars at the ARC, R. Kleynhans and S. Venter, Jul. 2012, pp. 1-23.*
UPOV Guidelines for the Conduct of Tests for Distinctness, Homogeneity and Stability for *Lachenalia*, TG/126/4 published Oct. 12, 1990, pulled from www.upov.int/edocs/tgdocs/en/tg126.pdf on Jan. 22, 2018 (Year: 1990).*
CPVO Variety Data Sheet for Application No. 20141911, Applicant: Agricultural Research Council, Application/Filing Date Jul. 29, 2014, published Oct. 15, 2014, 1 page, Community Plant Variety Office, France.
Certificate of Grant of Plant Breeder's Right, Registration No. ZA20104393, Applicant: ARC (Agricultural Research Council), dated Apr. 20, 2010, 1 page, Department of Agriculture Forestry and Fisheries, Republic of South Africa.
CPVO Variety Data Sheet for Application No, 20141910, Applicant: Agricultural Research Council, Application/Filing Date Jul. 29, 2014, published Dec. 15, 2014, 1 page, Community Plant Variety Office, France.
Certificate of Grant of Plant Breeder's Right, Registration No. ZA20104392, Applicant: ARC (Agricultural Research Council), dated Apr. 20, 2010, 1 page, Department of Agriculture Forestry and Fisheries, Republic of South Africa.
CPVO Variety Data Sheet for Application No. 20141912, Applicant: Agricultural Research Council, Application/Filing Date Jul. 29, 2014, published Oct. 15, 2014, 1 page, Community Plant Variety Office, France.
Certificate of Grant of Plant Breeder's Right, Registration No. ZA20104394, Applicant: ARC (Agricultural Research Council), dated Apr. 20, 2010, 1 page, Department of Agriculture Forestry and Fisheries, Republic of South Africa.
CPVO Variety Data Sheet for Application No. 20141915, Applicant: Agricultural Research Council, Application/Filing Date Jul. 29, 2014, published Dec. 15, 2014, 1 page, Community Plant Variety Office, France.
Certificate of Grant of Plant Breeder's Right, Registration No. ZA20104396, Applicant: ARC (Agricultural Research Council), dated Apr. 20, 2010, 1 page, Department of Agriculture Forestry and Fisheries, Republic of South Africa.
CPVO Variety Data Sheet for Application No. 20141914, Applicant: Agricultural Research Council, Application/Filing Date Jul. 29, 2014, published Dec. 15, 2014, 1 page, Community Plant Variety Office, France.
Certificate of Grant of Plant Breeder's Right, Registration No. ZA20104397, Applicant: ARC (Agricultural Research Council), dated Apr. 20, 2010, 1 page, Department of Agriculture Forestry and Fisheries, Republic of South Africa.
CPVO Variety Data Sheet for Application No. 20141913 Applicant: Agricultural Research Council, Application/Filing Date Jul. 29, 2014, published Dec. 15, 2014, 1 page, Community Plant Variety Office, France.
Certificate of Grant of Plant Breeder's Right, Registration No. ZA20104395, Applicant: ARC (Agricultural Research Council), dated Apr. 20, 2010, 1 page, Department of Agriculture Forestry and Fisheries, Republic of South Africa.
Co-Pending U.S. Appl. No. 14/756,801, inventor Kleynhans, R., filed Oct. 15, 2015. (Not Published).
Co-Pending U.S. Appl. No. 14/756,803, inventor Kleynhans, R., filed Oct. 15, 2015 (Not Published).
Co-Pending U.S. Appl. No. 14/756,802, inventor Kleynhans, R., filed Oct. 15, 2015 (Not Published).
Co-Pending U.S. Appl. No. 14/756,821, inventor Kleynhans, R., filed Oct. 19, 2015 (Not Published).
Co-Pending U.S. Appl. No. 14/756,819, inventor Kleynhans, R., filed Oct. 19, 2015 (Not Published).
Niederwieser, J.G., and Vcelar, B., "Regeneration of *Lachenalia* Species from Leaf Explants," *HortScience* 25(6):684-687, American Society for Horticultural Science, United States (1990).
Slabbert, M.M., and Niederwieser, J.G., "In vitro bulblet production of *Lachenalia," Plant cell Reports* 18:620-624, Springer-Verlag, Germany (1999).

* cited by examiner

*Primary Examiner* — Anne Marie Grunberg
(74) *Attorney, Agent, or Firm* — Sterne, Kessler, Goldstein & Fox P.L.L.C.

(57) ABSTRACT

A new and distinct form of *Lachenalia* plant characterized by a bulb plant type having a spreading growth habit of a height of 15-30 centimetres (cm) and width of 10-15 cm having a purple flower with cream tips, and green leave with maroon spots, further characterized in that the spots are fairly pronounced in that it has a good contrast.

2 Drawing Sheets

*LACHENALIA* JACQ. F. EX MURRAY PLANT NAMED 'RADIENT'

Figure 1:
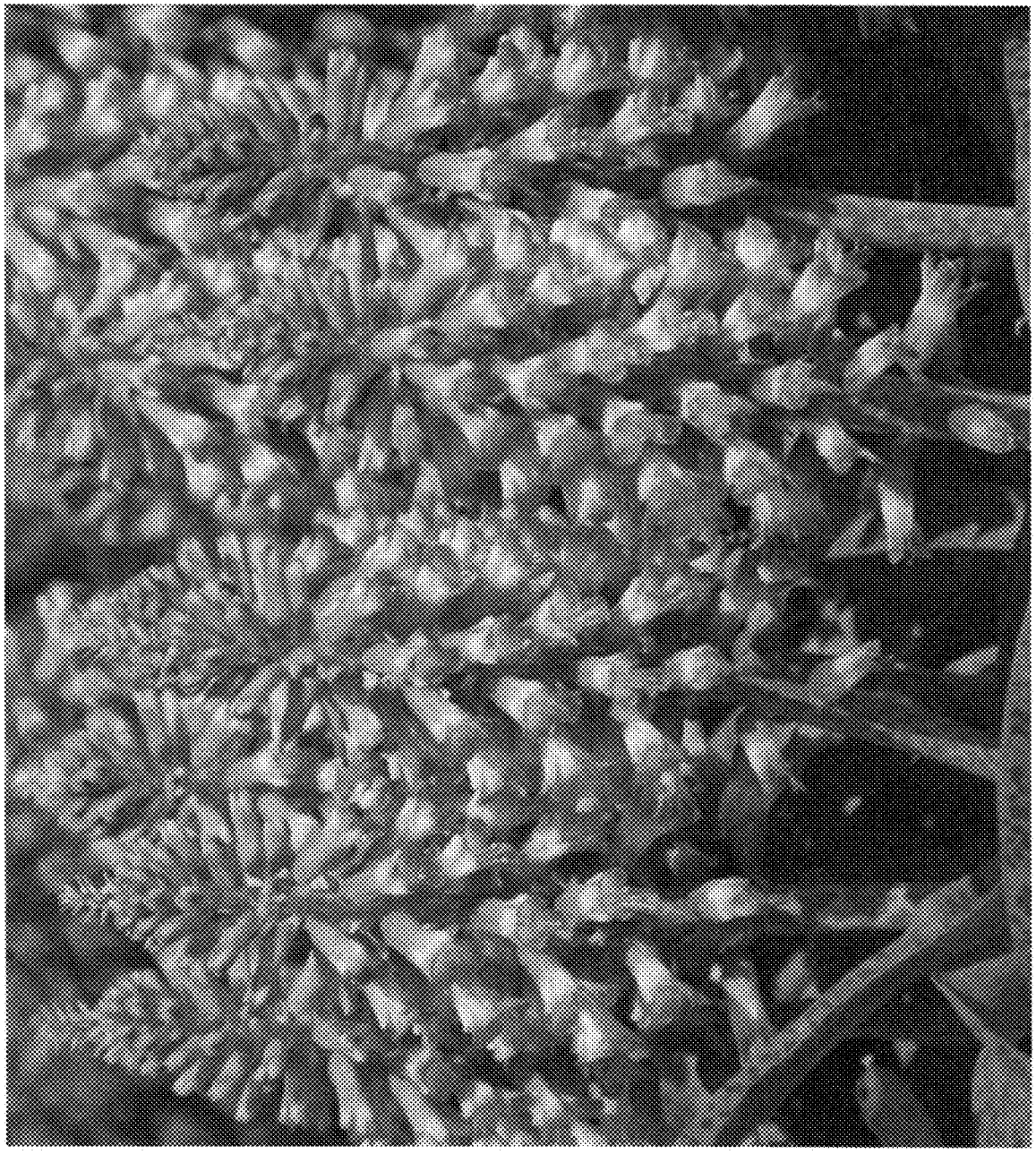
Figure 2:
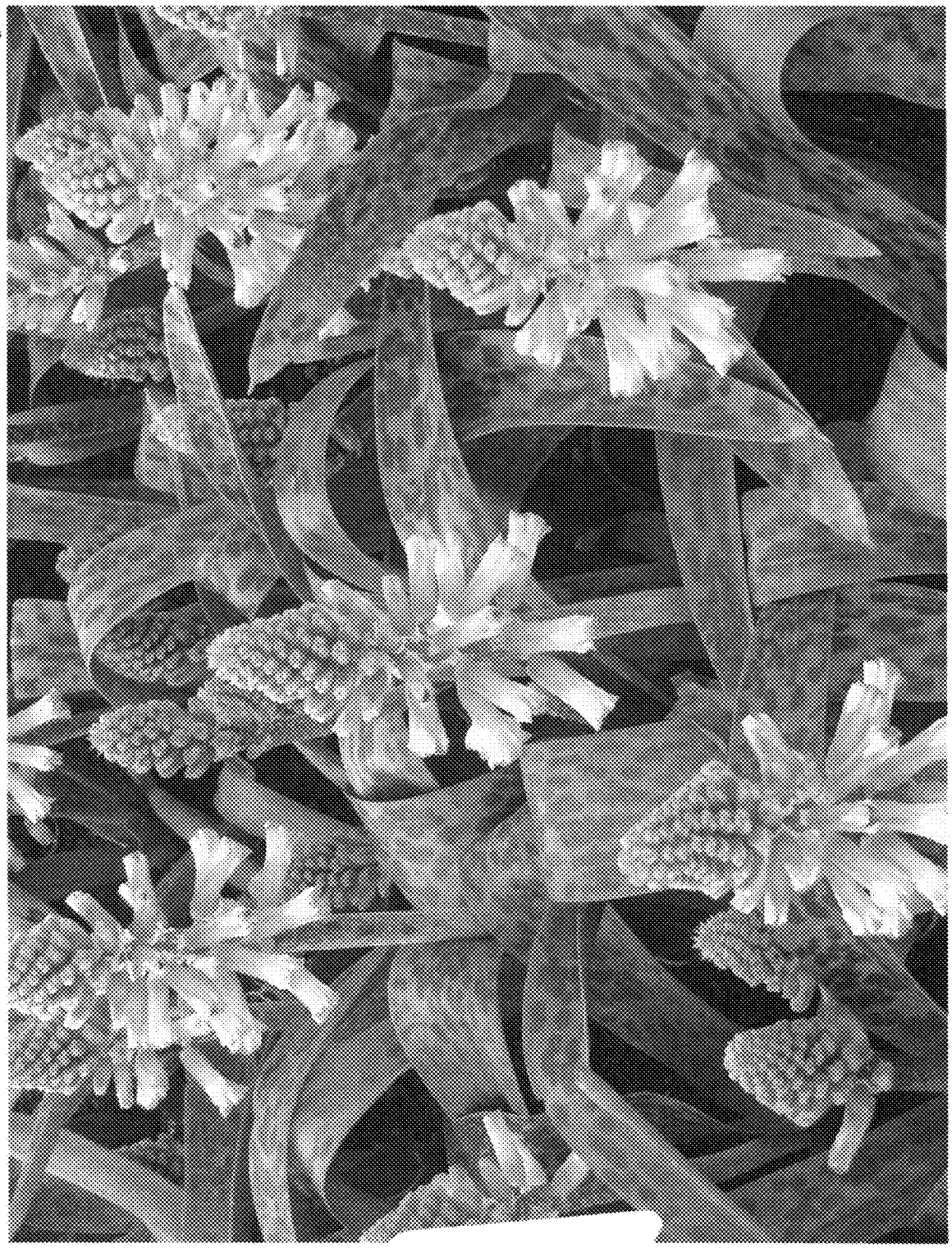

Genus and species: *Lachenalia* Jacq. f. ex Murray.
Variety denomination: 'Radient'.

BACKGROUND OF THE INVENTION

The present invention relates to a new and distinct cultivar of *Lachenalia*, botanically known as *Lachenalia* Jacq. f. ex Murray having the common name of Viooltjies/Cape cowslip and hereinafter referred to by its variety denomination 'Radient'.

The variety was first cultivated in 2008 and originated by means of induced mutation at the premises of Agricultural Research Council Vegetable and Ornamental Plant Institute, Roodeplaat, Pretoria, Republic of South Africa.

Asexual reproduction of the 'Radient' plant at the same location has shown that the unique features thereof are stable and reproduced true to type in successive generations of asexual reproduction.

SUMMARY OF THE INVENTION

The present invention constitutes a new and distinct variety of *Lachenalia* which originated from tissue culture as an induced mutation from the variety 'Rupert' as detailed hereinbelow and bred locally.

The following traits have been repeatedly observed and are determined to be the unique characteristics, under the local evaluation conditions, of the 'Radient' plant. These characteristics in combination distinguish 'Radient' as a new and distinct *Lachenalia* cultivar:

1. Bulb plant type having a spreading growth habit of a height of 15-30 centimetres (cm) and width of 10-15cm.
2. Flower color: purple (RHS #74C) with cream (RHS #8C) tips.
3. Leaf color: green (RHS #141C) with maroon (RHS #60A) spots.

Color references are made to The R.H.S. Color Chart, 1$^{st}$ edition, 1966, except where general color terms of ordinary significance are used or indicated otherwise.

Plants of the new *Lachenalia* variety 'Radient' can be compared to the denomination 'Rupert' but differs in that the flower color of 'Radient' is purple (RHS #74C) with cream (RHS #8C) tips compared to the purple only of 'Rupert'. 'Rupert' furthermore has a more blue-purple color at the base of the flower. The maroon (RHS #60A) spots of the 'Radient' plant is furthermore more pronounced in that they have a good contrast compared to the low contrast found in 'Rupert'.

Plants of the new *Lachenalia* variety 'Radient' can also be compared to similar denominations 'Winsome' and 'Leipoldt'.

'Winsome' has pinkish flowers compared to the purple (RHS #74C) color of 'Radient' and the tips of the flowers of 'Winsome' are purple-pink compared to the cream (RHS #8C) tips of 'Radient'. 'Winsome' has tubular flowers whilst the flowers of 'Radient' have spreading tips resulting in a denser appearance of the inflorescence of 'Radient'.

'Leipoldt' has pink flowers with dark purple tips. Although the flowers of 'Leipoldt' also have spreading tips, the density of 'Radient' is better than that of 'Leipoldt'.

BRIEF DESCRIPTION OF THE PHOTOGRAPHS

The first drawing illustrates the overall appearance of the 'Radient', showing the colors as true as it is reasonably possible to obtain in colored reproductions of this type. The first drawing comprises a front perspective view of a typical 'Radient' grown in an indoor nursery, but located in an outdoor setting.

The second drawing illustrates the overall appearance of the 'Radient', showing the colors as true as it is reasonably possible to obtain in color reproductions of this type. The second drawing comprises a front perspective view of a typical 'Radient' grown in an indoor nursery, but located in an outdoor setting.

DETAILED DESCRIPTION

The aforementioned drawings, following observations and measurements describe 'Radient' grown by the inventor on behalf of Agricultural Research Council Vegetable and Ornamental Plant Institute, Roodeplaat, Pretoria, Republic of South Africa. Thereafter 'Radient' was made subject of a South African Plant Breeders' Right application in March 2009. This application was granted in 2010 under number ZA20104395.

The plant is a late flowering cultivar and may be used for landscaping and should be planted during the month of March; indoors and in pots only. The plant should be kept at temperatures of 20-25 degrees Celsius during the day and 10-15 degrees Celsius at night. Plenty of light should be provided.

'Radient' is a mutant derived from the *Lachenalia* cultivar 'Rupert' through the use of irradiation. 'Rupert' is a hybrid-hybrid cross with the following species used in the hybrid crosses:

Female: [(*L. orchioides* subsp *glaucina* x *L. bulbifera*) selfed x (*L. orchioides* subsp *glaucina* x *L. rubida*) selfed]; and Male parent: [(*L. aloides* var quadricolor x *L. rubida*) x (*L. orchioides* subsp *glaucina*x *L. bulbifera*)selfed].

'Radient' was originally produced from irradiated leaf explant material. A specific plant displaying the flower colour mutation was selected from 20,000 plantlets and thereafter asexually propagated. The asexual progeny of this selection is the cultivar 'Radient' and was multiplied via tissue culture at the premises of Agricultural Research Council Vegetable and Ornamental Plant Institute, Roodeplaat, Pretoria, Republic of South Africa.

The following characteristics of 'Radient' are described with reference to description of said characteristic which are comparable with the mentioned variety/ies having said similar characteristic.

Leaf: Monocolored.

*Spots on upper side.*—Present and with good contrast.

| Characteristic: | Description of 'Radient': | Variety having similar characteristics: |
|---|---|---|
| Attitude: | Semi-erect | 'Romaud' |
| Length: | Short to medium - 17.5 cm | |
| Width: | Medium to wide - 5.8 cm | |
| Ratio: length/width | Large (elongated): 3:1 | 'Rodelein' |
| Shape: | Lanceolate | 'Rodelein' |
| Color: | Green (RHS #141C) | 'Roinge' |
| Leaf color designation for lower sides of the leaf | Green (RHS #141C) | |
| Shape in cross section: | Angular | 'Robyn', 'Romelia' |

-continued

| Characteristic: | Description of 'Radient': | Variety having similar characteristics: |
|---|---|---|
| Recurving of margin: | Absent | 'Eliza', 'Rodelein' |
| Undulation of margin: | Present | 'Elegant', 'Leipoldt' |
| Blistering and pubescence of upper side: | Absent | 'Rodelein', 'Rosabeth' |
| Spots on upper side: | Present (Maroon) (RHS #60A) | 'Bontrok', 'Roinge', 'Rosabeth' |
| Number of spots per leaf | Amount differs from plant to plant, no exact number of spots per leaf | |
| Size of spots on upper side: | Medium (2-3 millimeter (mm)) | 'Robyn', 'Roinge' |
| Density of spots on upper side: | Medium | 'Roinge', 'Rosabeth' |
| Intensity of spots on upper side: | Medium | 'Roline', 'Romelia' |
| Markings on outer side of leaf base: | Present | 'Roinge', 'Rozanne' |

Peduncle:

| Characteristic: | Description of 'Radient': | Variety having similar characteristics: |
|---|---|---|
| Length: | Short - 7.5 cm | 'Rolene', 'Romaud' |
| Peduncle color designation | Purplish (RHS #53B) with green (RHS #141C) | |
| Spots or markings: | Present | 'Bontrok', 'Rosabeth' |
| Coloration of peduncle spots | Purplish (RHS #53B) | |
| Size of spots or markings: | Medium (1-2 mm) | 'Robyn' |
| Density of spots or markings: | Medium, close to each other: spots may be as close as 0.2 mm, but may differ | 'Robyn' |

Bud:

| Characteristic: | Description of 'Radient': |
|---|---|
| Color | Purplish (RHS #53B) with green (RHS #141C) tips |

Inflorescense:

| Characteristic: | Description of 'Radient': | Variety having similar characteristics: |
|---|---|---|
| Length: | Medium - 15.7 cm | 'Robyn', 'Roklara' |
| Rudimentary apex: | Conspicuous | 'Ronette' |
| Number of flowers: | Many (±40-50 flowers) | 'Romaud', 'Sonni' |

Flower:

| Characteristic: | Description of 'Radient': | Variety having similar characteristics: |
|---|---|---|
| Description of floral organ | Inflorescence containing individual tubular flowers with spreading tips attached with pedicels to the peduncle | |
| Attitude: | Horizontal | 'Robyn', 'Romargo' |
| Pedicel: | Present | 'Romelia' |
| Length of pedicel: | Short to medium (2-3 mm) | |
| Length of flower: | Medium - 2.5 cm | 'Lizette', 'Rolene', 'Sonni' |
| Diameter excluding apex: | Medium - 0.7 cm | 'Romargo', 'Romelia', 'Rosabeth' |
| Diameter at apex: | Medium to large - 1.7 cm | |
| Attitude of distal part of inner perianth segments | Spreading | 'Rozanne' |
| Glossiness: | Absent | |
| Predominant color: | Purple (RHS #74C) with cream tips (RHS #8C) | 'Roklara' |
| Intensity of predominant color: | Medium to strong | |
| Outer perianth segment: color of basal part just before opening of flower | Violet-blue (RHS #-84A of RHS color chart, 2nd edition, 1986) | |
| Outer perianth segment: color of basal part of fully opened flower | Violet (RHS #87A of RHS color chart, 2nd edition, 1986) | |
| Outer perianth segment: color of apex relative to other part | Clearly different | 'Ronette' |
| Outer perianth segment: color of apex if clearly different from other part | Yellow-green (RHS #154A) | 'Bontrok', 'Leipoldt' 'Roinge' |
| Inner perianth segment: distinct spot in middle of apex | Present | 'Ronette' |
| Inner perianth segment: color of margin of apex relative to other part | Clearly different | 'Louis', 'Roinge' |
| Inner perianth segment: color of differently colored margin of apex | Purple (RHS #78B) | 'Leipoldt', 'Louis' |
| Inner perianth segment: predominant color of exposed part (excluding differently colored margin of apex) | Yellow (beige) (RHS #4D of RHS color chart, 2nd edition, 1986) | |
| Length of inner perianth segment compared to outer segments: | Longer | 'Roinge', 'Rosabeth' |
| Extrusion of stamens: | Absent | 'Roinge', 'Rosabeth' |
| Fragrance: | Present | 'Romaud' |
| Bulb: predominant shape: | Oblate | 'Romaud' |
| Time of flowering: | Medium - flowering time may vary from July to August (Southern Hemisphere) | 'Louis', 'Rozanne' |
| Duration of flowering: | Long (2 months) | 'Romelia', 'Rosabeth' |

Others:

| Characteristic: | Description of 'Radient': |
|---|---|
| Description of the bulb including size and color of the bulb at maturity | Cream/white (color designation - RHS #159C)<br>Size: between 1.5 to 2 cm in diameter |

-continued

| Characteristic: | Description of 'Radient': |
|---|---|
| Time of leaf growth/bud burst | Starts within the first week of watering (normally March/April in Southern Hemisphere) |
| A description of any fruit and seed set | No seed or fruit |
| Timing of leaf senescence | After flowering has completed and starts to die down, the leaves start to die off (wheat color) and plant dry out (September-October in Southern Hemisphere) |

The variety is not genetically modified and has been tested to be free of *Ornithogalum* Mosaic Virus.

The invention claimed is:

1. A new and distinct variety of *Lachenalia* plant named 'Radient' as illustrated and described herein.

* * * * *